United States Patent [19]

Hayes

[11] Patent Number: 4,909,067

[45] Date of Patent: Mar. 20, 1990

[54] STEAM QUALITY MEASUREMENT USING SEPARATING CALORIMETER

[75] Inventor: James K. Hayes, Chattanooga, Tenn.

[73] Assignee: Combustion Engineering, Inc., Windsor, Conn.

[21] Appl. No.: 264,267

[22] Filed: Oct. 28, 1988

[51] Int. Cl.$^4$ .................... G01F 15/08; G01N 15/00
[52] U.S. Cl. ......................................................... 73/29
[58] Field of Search ................ 73/19, 29, 53; 55/345, 55/398, 399

[56] References Cited

U.S. PATENT DOCUMENTS

| 17,675 | 6/1857 | Hale | 55/398 |
|---|---|---|---|
| 1,582,603 | 4/1926 | Hooper | 55/398 |
| 2,425,588 | 8/1947 | Alexander | 55/398 |
| 3,363,460 | 1/1968 | Baumann | 374/42 |
| 3,392,572 | 7/1968 | Brown | 73/29 |
| 3,413,838 | 12/1968 | Duddy | 73/29 |
| 3,430,483 | 3/1969 | Clawson et al. | 73/29 |
| 3,491,585 | 1/1970 | Hass | 73/29 |
| 3,596,516 | 8/1971 | Haynes, Jr. et al. | 73/29 |
| 3,971,252 | 7/1976 | Onoda | 394/41 |
| 4,149,403 | 4/1979 | Muldary et al. | 73/29 |
| 4,268,277 | 5/1981 | Rooker | 55/398 |
| 4,358,301 | 11/1982 | Chaix et al. | 55/345 |
| 4,455,095 | 6/1984 | Bleiker | 374/39 |
| 4,527,600 | 7/1985 | Fisher et al. | 141/4 |
| 4,561,785 | 12/1985 | Long et al. | 374/42 |
| 4,576,036 | 3/1986 | Huang et al. | 73/29 |
| 4,688,418 | 8/1987 | Cheung et al. | 73/29 |
| 4,769,593 | 9/1988 | Reed et al. | 73/29 |

OTHER PUBLICATIONS

ASME Performance Test Codes, Instruments and Apparatus, Part 11, Water and Steam in the Power Cycle (Purity and Quality, Leak Detection and Measurement), pp. 81-88.
Brochure, "Q:Bar Steam Quality Meter", EMCO, (5 pages).

Primary Examiner—Hezron E. Williams
Attorney, Agent, or Firm—Chilton, Alix & Van Kirk

[57] ABSTRACT

Wet stream is extracted isokinetically through a steam sampling nozzle and is directed, preferably vertically, through a moisture separating and divider unit (24) having a center tube (84) coaxially disposed in a substantially cylindrical shell (20), and a helical swirling device (98) coaxially located within the tube, which imparts centrifugal motion to the wet steam. As the steam passes through the helical device, the separated moisture droplets are drawn off from the vapor through holes (92, 94) in the periphery of the tube and fall to a liquid accumulator volume (26) in the shell. The extracted vapor is passed out of the shell to a measurement station including an orifice plate or venturi. Sensors (48, 50) are provided in the shell accumulator volume, to measure directly or indirectly, the mass of water extracted from the moisture separator. Similarly, the orifice plate and associated sensors (36, 38), measure the mass of vapor in the steam from which the liquid was extracted. Preferably, the orifice plate has differential pressure and absolute pressure sensors associated therewith for this purpose. Once the mass of liquid extracted from a known mass of total liquid and vapor is measured, the quality of the wet steam as sampled, is directly recorded indicated on a memory device (66).

18 Claims, 3 Drawing Sheets 4,909,067

STEAM QUALITY MEASUREMENT USING SEPARATING CALORIMETER

BACKGROUND OF THE INVENTION

The present invention relates to the measurement of the properties of steam, and more particularly to the on-line measurement of steam quality.

Accurate and reliable on-line measurement of steam quality is desired at a number of locations in power plants an petro chemical operations to monitor equipment performance, perform heat balances, and the like. The standard technique for determining steam quality utilizes throttling calorimeters and throttling separating calorimeters, in accordance with ASME Power Test Code 19.11 - 1970 Part II. These standard devices are not very suitable for continuous on-line measurement of steam quality. One of the disadvantages of throttling calorimeters and throttling separation calorimeters, is that the steam is normally discharged to atmospheric pressure where the steam sample is required. Thus, these devices are not generally used as "on-line" monitoring devices.

Recently, devices have appeared commercially which rely on the determination of steam density as an on-line indication of steam quality. In at least some instances, such devices may not be stable at, for example, 200 psia, and at higher pressures, such as 600 psig, their accuracy is still course, e.g., approximately ±5%. One example is described in International Patent Application No. PCT/US87/0276

U.S. patent application No. 141,556 filed Jan. 7, 1988 now U.S. Pat. No. 4,833,688 describes another technique for measuring steam quality which has the capability of improved performance over known devices, but it requires the heating of a sampling vessel and the maintenance of a high degree of insulation around the heated vessel.

SUMMARY OF THE INVENTION

Thus, a steam quality measurement device capable of accurate on-line performance over a wide range of pressure and quality, without the requirement for adding heat to a thermally insulated sampling vessel, would represent a significant improvement in this field of technology.

In accordance with the present invention, wet steam is extracted isokinetically through a steam sampling nozzle. The steam is directed, preferably vertically, through a moisture separating and divider unit. Preferably, the unit consists of a center tube coaxially disposed in a substantially cylindrical shell, and a helical swirling device coaxially located within the tube, which imparts centrifugal motion to the wet steam. As the steam passes through the helical device, the separated moisture droplets are drawn off from the vapor through holes in the periphery of the tube and fall to a liquid accumulator volume in the shell. The extracted vapor is passed out of the shell to a measurement station preferably including a venturi or an orifice plate.

Sensors are provided in the shell accumulator volume, to measure directly or indirectly, the mass of water extracted from the moisture separator. Similarly, the orifice plate and associated sensors, measure the mass of vapor in the steam from which the liquid was extracted. Preferably, the orifice plate has differential pressure and absolute pressure sensors associated therewith for this purpose.

Once the mass of liquid extracted from a known mass of total liquid and vapor is measured, the quality of the wet steam as sampled, is directly indicated.

BRIEF DESCRIPTION OF THE DRAWINGS

These and other objects and advantages of the invention are described below with reference to the accompanying figures, in which.

DESCRIPTION OF THE PREFERRED EMBODIMENT

Figure 1:
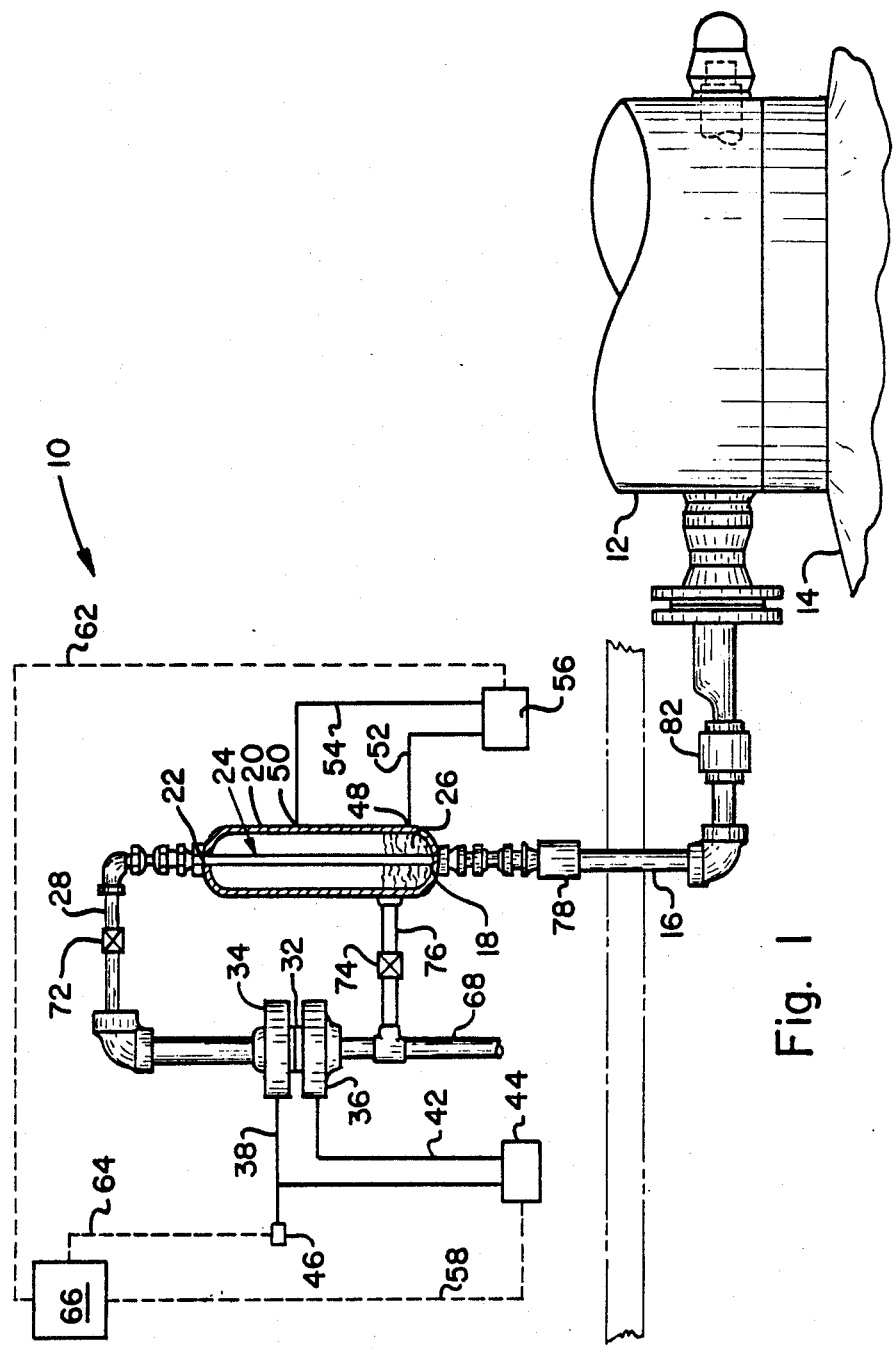
FIG. 1 is a schematic view of the steam quality measurement system of the present invention, connected to a sampling line for a main steam line.

FIG. 1 shows a steam quality measuring system 10 in accordance with the invention, connected to a main steam line 12, for example connected to the preseparation tank 14 of a nuclear steam generating system, through a steam sampling line 16. The sampling line 16 is fluidly connected to the inlet 18 of a pressure sealed, preferably vertically oriented shell 20, which has an outlet 22 spaced, preferably vertically, from the inlet 18. A moisture separator unit shown generally at 24 is located within the shell 20 between the inlet 18 and outlet 22. The space, preferably annular, between the separator unit 24 and the inner wall of the shell 20, defines an accumulator volume 26.

The moisture separator unit 24 extracts liquid from the wet steam passing through the sampling line 16 into the inlet 18. The separated liquid and the remaining vapor are divided and the extracted liquid is deposited in the accumulator volume 26. The vapor from the moisture separator is conveyed to the outlet 22, without mixing with the extracted liquid, and from there is removed from the shell 20.

An outlet pipe 28 carries the vapor to a vapor mass measuring station, preferably comprising an orifice plate 32 or venturi connected between upstream and downstream flanges 34, 36, respectively. An upstream pressure sensor 38 and a downstream pressure sensor 42 are associated with flanges 34, 36, respectively, and are connected to a differential pressure cell 44. Conveniently, an absolute pressure transducer 46 is also connected to the upstream flange 34, but the absolute pressure could be measured elsewhere in the steam quality measuring system 10. As is well known to those familiar with this technology, in a system assumed to contain saturated steam, the pressure as sensed at 46 also specifies the saturation temperature, and the differential pressure across a known orifice plate 32 uniquely measure the vapor mass flow rate.

The liquid extracted from the sampled steam which contained the measured vapor, accumulates in volume 26, which preferably is an annulus surrounding moisture separator unit 24. The level of the liquid in the accumulator volume 26 provides a direct indication of the volume of liquid that was extracted from the wet steam. Lower and upper sensor taps 48, 50 are fitted with signal lines 52, 54, respectively, which are connected to a differential pressure cell 56. The output of the differential pressure cell, when combined with knowledge of the temperature, is used to determine the mass of the liquid in the accumulator volume 26.

The output line 58 from the vapor flow differential pressure cell 44, the signal line 62 from the liquid level differential pressure cell 56, and the line 64 in which a signal indicative of the saturation temperature is obtained, are delivered to a central computer or local processor 66 which computes the steam quality, q, from the equation $q = w_v/(w_v + w_l)$ The valuable $w_v$ is the vapor mass or mass flow rate and $w_l$ is the liquid mass or mass flow rate. The quantity q is preferably displayed at the central computer or local processor 66.

It should be appreciated that the raw pressure and differential pressure signals on lines 58, 62 and 64 can be delivered to the computer 66 for appropriate preprocessing prior to the calculation of the quality, or the preprocessing, for example, conversion of differential pressure to a quantity of mass in the accumulator volume 26, can be performed by a preprocessor associated with the instrumentation, e.g., differential pressure cell 56. In order to assure optimum performance, the shell 20, outlet pipe 28, flanges 34, 36, orifice plate 32 are thoroughly insulated.

After exiting the plate 32 and flange 36, the vapor flows through return line 68 to the main steam line 12, at a point downstream of sampling line 16 and past sufficient valves and fittings in the steam line 12 to assure that adequate differential pressure exists to achieve isokinetic steam sampling. This should be confirmed initially, by performing hydraulic calculations as is known to practitioners in this field of technology.

In the preferred embodiment, a solenoid valve 72 is located in the outlet pipe 28, and another solenoid valve 74 is located in a drain pipe 76 connected between the outlet of flange 36 or the return line 68, and the accumulator volume 26 through shell 20. When the upper solenoid valve 72 is closed and the lower solenoid valve 74 is opened, the accumulator volume 26 can be drained of liquid. Preferably, a ball valve 78 is provided between the sampling line 16 and the inlet 18 of the shell 20, so that the steam sample may be directed to a throttling calorimeter (not shown) as a check or calibration in the event the steam quality is thought to fall within the accurate range of a throttling calorimeter.

More generally, the operation of the device in accordance with the invention proceeds as follows. One or more of the isolation valves 82 at the connection to the main steam line 12 is opened, thus permitting sample steam flow to be directed through the sampling line 16. The initial liquid level in the accumulator volume 26 is measured by means of the differential pressure cell 56. This establishes the reference value at the start of the quality measurement cycle the The extracted liquid level can then be monitored to determine the liquid extraction rate (lbs/hr), or total mass accumulated over a specified period of time. The vapor flow rate (lbs/hr) is measured by the differential pressure cell 44 and pressure transducer 46, for the same time period as the liquid extraction rate is monitored. This information is sufficient for the computation of the steam quality. When the liquid level in accumulator volume 26 approaches the upper tap 50, the upper solenoid valve 72 is closed and the lower solenoid valve 74 is opened, thus draining the accumulator volume 26 of liquid. The drop in the liquid level is monitored, and, when the liquid level approaches the lower tap 48, the upper valve 72 is opened and the lower valve 74 is closed so that the determination of steam quality can begin again.

Alternatively, when a specific level change, for example one inch, occurs in the accumulator volume 26, the steam quality is computed. The computer could then store and/or display intermittent steam quality per inch of accumulated liquid volume and mean steam quality as a function of accumulated volume.

Figure 2:
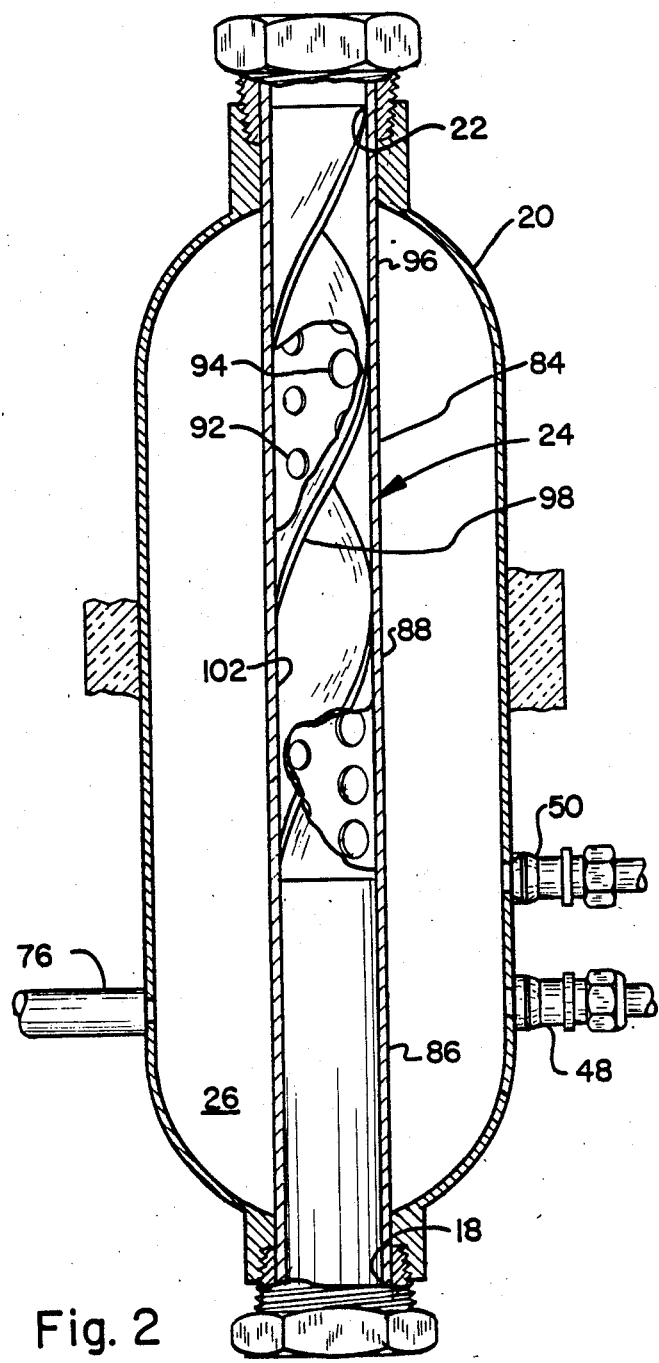
FIG. 2 is a detailed view of the preferred steam separator unit for use with the system as shown in FIG. 1.

FIG. 2 shows the preferred structure constituting the moisture separator unit 24. A central tube 84 extends from the inlet 18 vertically to the outlet 22 and, although other shapes are possible, is conveniently cylindrical. In a typical implementation of the invention, the shell 20 would have a cylindrical main body portion made from, for example, four inch schedule 40 pipe, and upper and lower closures in which the inlet 18 and outlet 22 are formed. The cylindrical length of the shell 20 would conveniently be approximately 36 inches. The central tube 84 preferably has three portions. The lower portion 86 extends from the inlet 18 to approximately the level of the upper pressure tap 50, and has an imperforate wall. The intermediate extraction portion 88 has a length of approximately nine inches, and a multiplicity of 0.19 inch diameter and 0.25 inch diameter radial holes 92 spaced on a substantially triangular pitch. The upper, vapor conduit portion 96 is imperforate and connected to the shell outlet 22. The central tube 84 can conveniently be made from 0.75 inch OD tubing. From approximately the inlet 18, or from the elevation of the upper level tap 50, to the outlet 22, a moisture separator in the form of a helical swirler 98, is formed with approximately one revolution per six inches in length. The swirler 98 is coaxial with, and substantially the same circumference as, the inner wall 102 of tube 84. As the sample steam encounters the swirler 98, the relatively heavy moisture is thrown radially outwardly and impinges on the inner surface 102 of the tube 84. The holes 92, 94 in the intermediate tube portion 88 convey the extracted liquid out of the tube, thereby progressively dividing the liquid from the vapor. The less dense vapor tends to remain axially centered within the swirling steam, and is eventually conveyed through the conduit potion 96, in outlet 22, to the orifice plate 32 as shown in FIG. 1. The liquid passing through the holes 92, 94 falls through the space between the tube 84 and the shell 20, or drips down along the tube outer wall, and accumulates in the volume 26.

Air water tests have indicated that the moisture separation arrangement, i.e., the swirler 98 and the central tube 84 arrangement shown in FIG. 2, is effective to the extent that the steam quality in the outlet pipe 28 will be approximately 99%. Information from technical literature such as the article "Metering of Wet Steam" by D. Chisolm et al, *Chemical and Process Engineering,* July 1969 indicates that the error in determination of steam mass flow is essentially negligible (less than 1%) for steam quality in the range 98%–100%.

The separator configuration essentially removes all moisture where inlet steam quality is in the range 70–99% and wet steam velocity is up to about 16 ft/sec. Thus, the steam entering the orifice or venturi 32 (FIG. 1) would normally be dry saturated steam.

For use outside the optimum steam separation range of the separator unit 24, laboratory calibration tests can establish the efficiency of the moisture separation device as a function of flow rate and steam quality, which can be accounted for in the computer 66. Similarly, it would be feasible to establish orifice plate correction factors to be utilized in the steam flow rate calculations if the correction factors are significant.

A dedicated control panel (not shown) can be provided for mounting the computer 66 which, in addition to the functions described above, can also monitor the liquid level in the accumulator volume 26, and perform the logic steps, such as opening and closing the solenoid valves, as required to periodically cycle the steam quality measuring system 10 through the measuring and draining cycles. Furthermore, the computer can be connected to display devices or other logging equipment.

Figure 3:
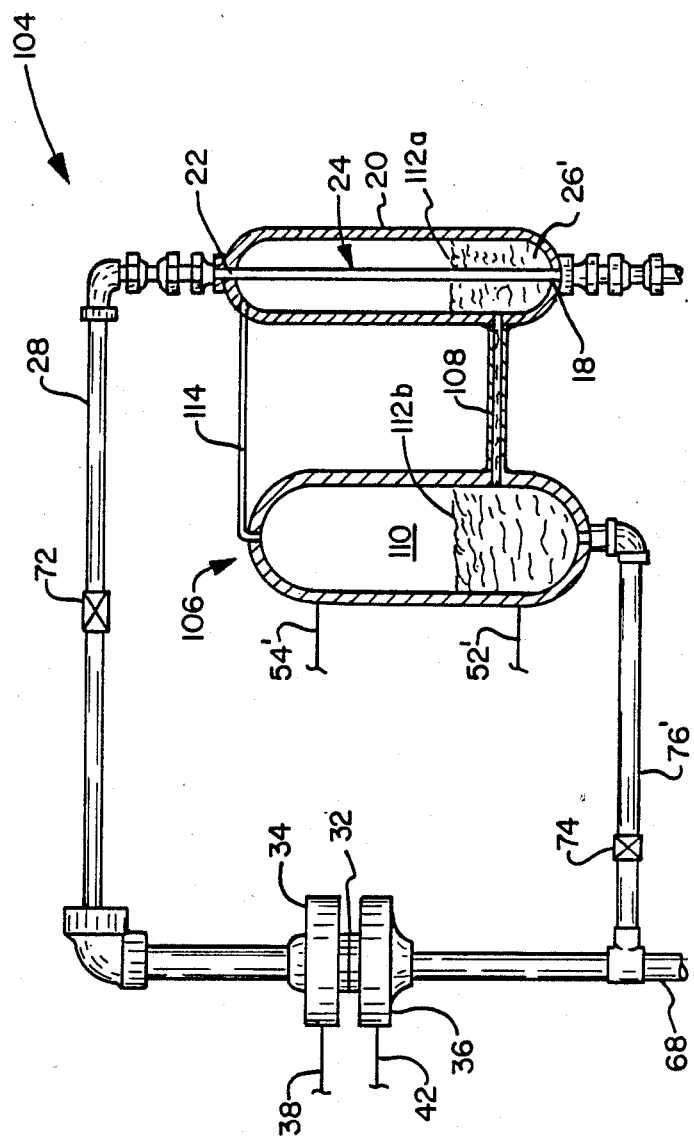
FIG. 3 is a schematic view of an alternative embodiment of the system shown in FIG. 1, adapted for use in measuring low quality steam.

FIG. 3 shows an alternative embodiment of a steam quality measuring system 104 in which the liquid accumulation 26' is augmented by a vessel or chamber 106 external to the shell 20, but in fluid communication therewith through liquid balancing line 108. The vessel 106 defines a supplementary accumulator volume 110 which is fluidly connected to accumulator volume 26' through pipe 108. The liquid extracted through separator 24 initially accumulates in the volume 26', but the liquid level 112a in shell 20 is, in effect, reproduced as level 112b in vessel 106, as a result of the pipe 108 and the pressure balance line 114.

In the embodiment of FIG. 3, the pressure lines 52, 54 associated with the shell 20 as shown in FIG. 1, can be associated with the vessel 106 as pressure sensor lines 52', 54'. Similarly, the drain line 76 shown in FIG. 1 is connected between return line 68 and the vessel 106.

The embodiments shown in FIGS. 1 and 3 are substantially functionally equivalent, but the embodiment of FIG. 3 would preferably be used in steam supply systems having low quality, i.e., below about 70%. In such low quality environments, the rate of liquid extraction by separator 24 is quite rapid and the water level rise within shell 20 may be more rapid than is desired. Thus, by providing a larger accumulation volume 110 in which the water level 112b rises proportionately to that in 112a, the rate of water level rise may, in effect, be slowed somewhat for greater compatibility with operating and control time cycles for the plant and technicians. For example, in the embodiment of the arrangement shown in FIG. 1, wherein the useful measurement height range in the accumulator volume 26 may be about 20 inches, steam flowing through separator unit 24 will typically be extracted at the rate of 127 seconds for a level rise of one inch in the accumulator volume 26. At 70% steam quality, the period for the water level to rise one inch is about 21 seconds.

It can be appreciated that a user who has purchased a steam quality measuring system of the type shown in FIG. 1, and may later wish to employ it in an environment with steam quality lower than 70%, may easily add the augmentation vessel 106, without the need to change or modify the existing components.

Other varieties of steam separator units 24 could be substituted for the preferred embodiment shown in FIG. 2. For example, my copending patent application U.S.S.N. 151,012, now Pat. No. 4,856,461 Multiple Tube Steam Dryer for Moisture Separator Reheater, the disclosure of which is hereby incorporated by reference, describes other potentially suitable steam separator units 24 that can be adapted for use in the present invention.

I claim:

1. Apparatus for measuring steam quality, comprising:
   an elongated, pressure sealed shell having spaced apart inlet and outlet at the longitudinal ends of the shell, the inlet adapted for connection to a steam sampling line;
   substantially helical moisture separator means located longitudinally within the shell and in fluid communication with the inlet, for separating liquid from vapor in the stream that enters the shell through the inlet;
   a tubular member surrounding the moisture separator means and extending longitudinally within the shell, said tubular member having portions including,
   divider means for conveying the liquid from the moisture separator means;
   means cooperating with the shell for defining an accumulator volume within the shell, where the conveyed liquid can accumulate;
   conduit means for conveying the separated vapor to the outlet;
   means for measuring a first variable commensurate with the mass of the separated vapor that exits the shell through the outlet;
   means for measuring a second variable commensurate with the mass of the liquid in the accumulator volume associated with said mass of separated vapor; and
   means responsive to the means for measuring the first and second variables, for determining the quality of the steam in the sampling line.

2. The apparatus of claim 1, wherein
   the tubular member has one end defining said conduit means,
   the means for defining the accumulator includes the tube other end fluidly connected to the inlet, and
   the divider means includes a tube extraction portion intermediate the tube ends, the extraction portion including an inner surface onto which the radially outer, substantially liquid portion of the swirling steam impinges.

3. The apparatus of claim 2, wherein the shell and tube are vertically oriented, the portion of the tube constituting said divider means includes an imperforate tube lower portion below said tube extraction portion, and the tube extraction portion is perforated for passing the conveyed liquid from the tube inner surface to the accumulator volume.

4. The apparatus of claim 3, wherein the lower portion of the tube and an adjacent, radially spaced portion of the shell define said accumulator volume.

5. A system for measuring steam quality in a main steam line through a steam sampling line, comprising:
   a main steam line, having steam flow passing continuously therethrough;
   a sampling line connected to the main steam line for isokinetically diverting a sample steam flow from the main steam line while steam flows through the main steam line;
   a pressure sealed shell having spaced apart inlet and outlet openings, the inlet opening being connected to the steam sampling line:
   a moisture separator unit located within the shell and fluidly connected between the inlet and outlet, including means for separating liquid from vapor in the steam that enters the shell through the inlet opening by imparting a swirling flow pattern to the steam, means for defining with the shell, an accumulator volume into which the separated liquid is deposited and means for conveying the separated vapor to the outlet opening;

means for measuring a first variable commensurate with the mass of the separated vapor that exits the shell through the outlet opening;

means for measuring a second variable commensurate with the mass of the liquid in the accumulator volume; and means responsive to the means for measuring the first and second variables, for determining the quality of the steam in the sampling line.

6. The apparatus of claim 5, wherein the shell is in the form of an elongated, vertically oriented cylinder.

7. The apparatus of claim 5, further including an auxiliary accumulator chamber external to the shell, in fluid communication with said accumulator volume.

8. The apparatus of claim 5, wherein the moisture separator unit includes, a tube surrounding the means for imparting a swirling flow pattern, and the accumulator volume is defined by the tube exterior and the shell.

9. The apparatus of claim 8, wherein the means for imparting a swirling flow pattern includes an elongated helix, the shell and tube are vertically oriented, and the tube contains the helix and includes an imperforate tube lower portion and an upper tube extraction portion that is perforated for conveying the liquid from the swirling flow pattern to the accumulator volume.

10. The apparatus of claim 9, wherein the lower portion of the tube and an adjacent, radially spaced portion of the shell define said accumulator volume.

11. The apparatus of claim 6, wherein the means for measuring the second variable include means for measuring the level of liquid in the accumulator volume.

12. The apparatus of claim 5, including first valve means located in the means for conveying the separated vapor, a return line connected to deliver the vapor from the means for measuring the mass of the vapor to the main steam line, a drain pipe fluidly connected between the return line immediately downstream of the means for measuring the mass of the separated vapor and the accumulator volume of the shell, and second valve means located in the drain pipe.

13. A method for measuring the quality of steam in a main steam line, comprising the steps of:

isokinetically drawing a flow of sample steam from the main steam line while steam flow continues in the main steam line;

passing the sampled steam through a moisture separator unit which imparts a swirling flow pattern to the steam;

measuring a first variable commensurate with the mass of vapor extracted by the separator unit;

measuring a second variable commensurate with the mass of liquid extracted by the separator unit; and from said measurements of the first and second variables, determining the fraction of the total mass of the sampled steam that is contributed by vapor.

14. The method of claim 13, wherein, the step of measuring the second variable includes accumulating the extracted steam in an accumulator volume formed in part by the moisture separator unit.

15. The method of claim 14, further including the steps of:

substantially draining the accumulator volume, accumulating liquid in the accumulator volume and determining when the accumulator volume is substantially full, draining the accumulator volume when the accumulator volume is substantially full, repeating the steps of draining and accumulating, and determining said fraction and recording the fraction in a memory device remote from the unit, for each of a plurality of occurrences of a full accumulator volume.

16. The method of claim 14, wherein the steps of measuring the first and second variables are performed while the liquid level in the accumulator volume is increasing.

17. The method of claim 15, wherein the step of draining the accumulator volume includes, blocking the flow of vapor extracted by the separator unit, and opening a flow path from the accumulator volume to a point in the steam line downstream of the point in the steam line where the sample stream is drawn.

18. The method of claim 13, wherein the step of measuring the second variable includes, accumulating a first portion of the extracted liquid in a first accumulator volume defined by a first vessel containing said moisture separator unit, and accumulating a second portion of the extracted liquid in a second accumulator volume defined by a second vessel that is in pressure balanced fluid communication with said first accumulator volume.

* * * * *